United States Patent
Al-Noor et al.

(10) Patent No.: US 11,464,477 B2
(45) Date of Patent: Oct. 11, 2022

(54) BLOOD VESSEL OBSTRUCTION DIAGNOSIS METHOD, APPARATUS AND SYSTEM

(71) Applicant: THINKSONO LTD, London (GB)

(72) Inventors: Fouad Al-Noor, London (GB); Sven Mischkewitz, London (GB); Antonios Makropoulos, London (GB); Ryutaro Tanno, London (GB); Bernhard Kainz, London (GB); Ozan Oktay, London (GB)

(73) Assignee: THINKSONO LTD, London (GB)

( * ) Notice: Subject to any disclaimer, the term of this patent is extended or adjusted under 35 U.S.C. 154(b) by 32 days.

(21) Appl. No.: 16/491,553

(22) PCT Filed: Mar. 6, 2018

(86) PCT No.: PCT/GB2018/050559
§ 371 (c)(1),
(2) Date: Sep. 5, 2019

(87) PCT Pub. No.: WO2018/162888
PCT Pub. Date: Sep. 13, 2018

(65) Prior Publication Data
US 2021/0128099 A1    May 6, 2021

(30) Foreign Application Priority Data

Mar. 6, 2017 (GB) .................................. 1703575
Feb. 9, 2018 (GB) .................................. 1802211

(51) Int. Cl.
*A61B 8/06* (2006.01)
*G16H 40/67* (2018.01)
(Continued)

(52) U.S. Cl.
CPC ............... *A61B 8/06* (2013.01); *A61B 8/085* (2013.01); *A61B 8/0833* (2013.01);
(Continued)

(58) Field of Classification Search
CPC ...... G16H 50/20; A61B 8/467; A61B 8/0891; A61B 8/085; A61B 8/0833
See application file for complete search history.

(56) References Cited

U.S. PATENT DOCUMENTS

| 4,721,113 A | 1/1988 | Stewart et al. |
| 6,358,208 B1 | 3/2002 | Lang et al. |

(Continued)

FOREIGN PATENT DOCUMENTS

| CN | 1765330 A | 5/2006 |
| CN | 1914617 A | 2/2007 |

(Continued)

OTHER PUBLICATIONS

International Search Report and Written Opinion received for Patent Application No. PCT/GB2018/050559, dated Jul. 4, 2018. 13 pages.

(Continued)

*Primary Examiner* — Amanda Lauritzen Moher
*Assistant Examiner* — Sean V Blinder
(74) *Attorney, Agent, or Firm* — Finch & Maloney PLLC

(57) ABSTRACT

The present disclosure relates to a method and system for diagnosing blood vessel obstruction, such as would occur in deep vein thrombosis (DVT). More specifically, the present disclosure relates to a software tool for use with sensor hardware to allow users to perform standardised and repeatable testing of patients to assist with diagnosis of deep vein thrombosis or related conditions. The present disclosure further relates to an apparatus and method for conducting the diagnosis. The apparatus includes an imaging probe and a computing device, where the computing device is config- (Continued)

ured to assist the user in placing the imaging probe on a blood vessel and moving the imaging probe between predetermined landmarks along the blood vessel.

20 Claims, 13 Drawing Sheets

(51) Int. Cl.
*G16H 50/30* (2018.01)
*G16H 50/20* (2018.01)
*G16H 30/40* (2018.01)
*A61B 8/00* (2006.01)
*A61B 8/08* (2006.01)
*G06N 3/08* (2006.01)

(52) U.S. Cl.
CPC ............ *A61B 8/4472* (2013.01); *A61B 8/461* (2013.01); *A61B 8/467* (2013.01); *A61B 8/488* (2013.01); *A61B 8/54* (2013.01); *A61B 8/56* (2013.01); *G06N 3/08* (2013.01); *G16H 30/40* (2018.01); *G16H 40/67* (2018.01); *G16H 50/20* (2018.01); *G16H 50/30* (2018.01)

(56) References Cited

U.S. PATENT DOCUMENTS

| | | | |
|---|---|---|---|
| 6,589,164 | B1 | 7/2003 | Flaherty |
| 8,629,888 | B1 | 1/2014 | Chen et al. |
| 9,700,219 | B2* | 7/2017 | Sharma ................ A61B 5/026 |
| 2007/0016072 | A1* | 1/2007 | Grunwald ............... A61B 5/02 600/468 |
| 2008/0269605 | A1* | 10/2008 | Nakaya ............... A61B 5/6844 600/437 |
| 2009/0093807 | A1 | 4/2009 | Hyde et al. |
| 2011/0098564 | A1 | 4/2011 | Larson et al. |
| 2012/0203093 | A1 | 8/2012 | Imran et al. |
| 2012/0296214 | A1* | 11/2012 | Urabe ................ A61B 8/0858 600/444 |
| 2014/0249405 | A1 | 9/2014 | Wimer |
| 2015/0112182 | A1 | 4/2015 | Sharma et al. |
| 2015/0272538 | A1 | 10/2015 | Millett |
| 2016/0135757 | A1* | 5/2016 | Anderson ............ A61B 5/7475 600/407 |
| 2016/0174902 | A1* | 6/2016 | Georgescu ............ G06T 7/0012 600/408 |
| 2017/0181726 | A1* | 6/2017 | Schneider ................ A61B 8/54 |
| 2019/0239848 | A1* | 8/2019 | Bedi ...................... A61B 5/742 |

FOREIGN PATENT DOCUMENTS

| | | |
|---|---|---|
| CN | 101208045 A | 6/2008 |
| CN | 101351157 A | 1/2009 |
| CN | 101854853 A | 10/2010 |
| CN | 102512206 A | 6/2012 |
| CN | 102763122 A | 10/2012 |
| CN | 103337096 A | 10/2013 |
| CN | 104224129 A | 12/2014 |
| CN | 104398271 A | 3/2015 |
| CN | 104706382 A | 6/2015 |
| CN | 105228518 A | 1/2016 |
| CN | 105389810 A | 3/2016 |
| CN | 105636644 A | 6/2016 |
| CN | 106456016 A | 2/2017 |
| GB | 2419403 A | 4/2006 |
| JP | 2000229078 A | 8/2000 |
| JP | 2008272025 A | 11/2008 |
| JP | 2015061591 A | 4/2015 |
| JP | 2016116605 A | 6/2016 |
| WO | 2006061829 A1 | 6/2006 |
| WO | 2013005179 A1 | 1/2013 |
| WO | 2014097090 A1 | 6/2014 |
| WO | 2015087218 A1 | 6/2015 |
| WO | 2015150932 A1 | 10/2015 |
| WO | 2016075586 A1 | 5/2016 |
| WO | 2016141449 A1 | 9/2016 |
| WO | 2018162888 A1 | 9/2018 |

OTHER PUBLICATIONS

Combined Search and Examination Report under Sections 17 and 18(3) received for GB Application No. 1703575.9, dated Sep. 6, 2017. 9 pages.
Office Action received for JP Application No. 2019-548952 (corresponds to U.S. Appl. No. 16/491,553), dated Nov. 2, 2021. 5 pages with translation.
CN First Notification of Office Action, CN Application No. 2018800161762, dated Dec. 1, 2021. 17 pages.
Notification on The Grant for Patent Right for Invention and references therein received for CN App. No 201880016176.2, dated Aug. 3, 2022. 7 pages including 1 page of translation.

* cited by examiner

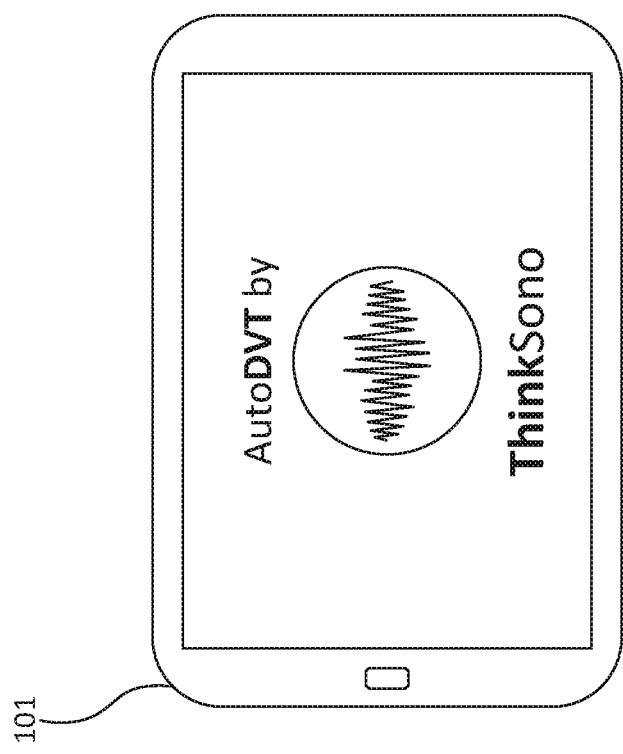
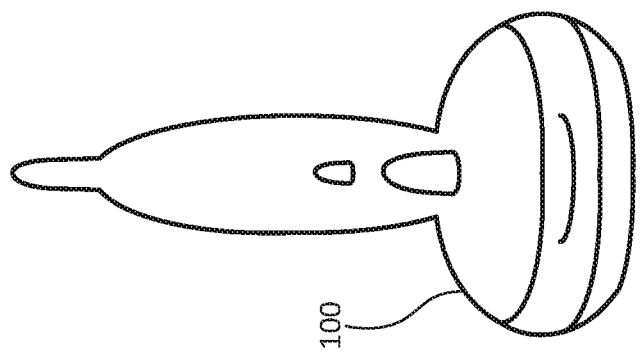
Figure 1

BLOOD VESSEL OBSTRUCTION DIAGNOSIS METHOD, APPARATUS AND SYSTEM

FIELD

The present invention relates to a method and system for diagnosing blood vessel obstruction, such as would occur in deep vein thrombosis (DVT). More specifically, the present invention relates to a software tool for use with sensor hardware to allow users to perform standardised and repeatable testing of patients to assist with diagnosis of deep vein thrombosis or related conditions. The present invention further relates to an apparatus and method for conducting the diagnosis.

BACKGROUND

Typically, an average of one in a thousand people will be affected by deep vein thrombosis (hereafter referred to as "DVT") and related conditions. In the United Kingdom, approximately 100,000 people are admitted to hospital each year due to DVT or a related condition and 20,000 people die due to undiagnosed DVT or a related condition. Worldwide, approximately 10 million people suffer from DVT or related conditions.

Patients tend to be referred for DVT-specific tests by front line medical professions, such as general practitioners, nurses, accident and emergency departments or following other medical care such as post-surgery. As the risk from DVT to patients is deemed to be high, i.e. there is a high probability of death, if there is any suspicion that a patient might be at risk from DVT or might be susceptible to DVT then there is a high likelihood that the frontline medical professionals will refer patients for DVT-specific tests where sufficient symptoms of DVT are exhibited. Further, there is a need to monitor patients who have undergone recent surgery for DVT as the probability of a patient having DVT increases substantially following surgery).

The routine method used to diagnose DVT is through use of a D-dimer blood test, to determine the concentration of a small protein fragment in the blood that occurs when a blood clot is degraded by fibrinolysis, and an ultrasound scan. A patient with DVT symptoms is typically sent for an ultrasound examination, carried out by a specialist in a hospital, who can confirm the condition to a sufficiently high degree of accuracy. In most cases, a D-dimer blood test is performed before an ultrasound examination is performed.

To get a confirmed diagnosis to a sufficient reliability however, an ultrasound examination needs to be performed and it should be performed by a DVT specialist. One reason for this is that the D-dimer blood test can with high certainty rule out a pulmonary embolism (hereafter referred to as a PE). As many patients with DVT progress on to having a PE, which is a main cause of death for those with DVT, the D-dimer test is useful for detecting if there is a risk of PE. However, the D-dimer test has a high sensitivity to PE but a low specificity as to how much of a risk there is—i.e. it can only conclusively indicate if there is no risk of a PE as if the test returns a negative result there is a very low probability that the patient with develop a PE. If the D-dimer test returns a positive result, then the patient may have DVT or many other conditions—the test can frequently return a positive result for many different reasons and hence the patient is almost always then sent for an ultrasound scan with a DVT specialist following a positive result.

As the only route to gaining a sufficiently reliable confirmed diagnosis for DVT, the number of patients referred for an ultrasound scan with a DVT specialist and the consequent workload can be very large relative to the number of specialist DVT radiologists in a hospital. Of the patients referred, many of those referred result in a negative diagnosis for DVT despite the high numbers of patients referred having positive results from the D-dimer blood test. Thus, this false positive rate leads to significant costs, due to the need for specialist staff and equipment to be used for large numbers of tests, and inefficiency due to the high false positive rate. For example, in 2004 for the UK it was estimated that £640 million per year is spent tackling the combination of DVT and PE (together called Venous Thromboembolism or VTE) while for the US it was estimated in 2011 to cost $10 billion per year.

Following a diagnosis of DVT being confirmed by an ultrasound scan performed by a DVT specialist radiologist, typically patients are prescribed an anticoagulation drug (for example Heparin or Warfarin) for a period of anywhere between 3 months and for the rest of their lives.

For frontline medical professionals, it is difficult to assess DVT more accurately as the symptoms overlap with other less serious conditions.

For patients, it can be difficult to attend appointments with specialist DVT radiologists as these practitioners are typically only based in larger hospitals serving large catchment areas so patients can struggle to get to these hospitals for appointments to get a definitive diagnosis, only for most patients not to be diagnosed with DVT due to the high false-positive rate of the D-dimer test. Sometimes patients in remote areas do not have access to the required specialist staff and/or equipment. In other cases, patients experience significant delays before being seen at the hospital due to limited numbers of specialist staff and/or limited availability of equipment—this can lead to problems monitoring, for example, post-surgery patients.

Patients who are unable or do not attend appointments with specialist DVT radiologists are typically prescribed an anticoagulant for preventative treatment but without any certainty that a DVT diagnosis based on only a D-dimer test is correct, thus such a prescription being in many cases unnecessary. This is especially the case for patients who are visited by frontline staff, who are unable to attend an appointment with a specialist at a hospital, for example residents in nursing homes—the frontline staff can't diagnose DVT as they do not have the expertise or equipment, so can only prescribe or arrange a prescription for preventative medication. In some cases, an inappropriate prescription of anticoagulants can increase the risk of bleeding for patients with specific conditions or other undiagnosed conditions such as advanced age (patients aged over 65 years old), cancer, renal failure, liver failure, co-morbidity and reduced functional capacity.

SUMMARY OF INVENTION

Relatively inexpensive ultrasound machines, typically handheld, have more recently become available. These cheaper and/or smaller ultrasound machines can be used to diagnose DVT and related conditions but only when used by a specialist and/or when a specialist radiologist interprets the ultrasound images properly.

The present invention relates to a method and system that can be used with ultrasound equipment, including but not limited to these more recently available inexpensive and/or smaller ultrasound machines, to assist non-specialists with using ultrasound equipment to perform ultrasound examinations and/or with assisting non-specialists to diagnose (or not) patients to a substantially high level of accuracy—in particular in relation to performing ultrasound examinations for DVT and/or diagnosing DVT (or related conditions).

According to a first aspect of the present invention, there is provided an apparatus for diagnosing whether a blood vessel is obstructed, comprising: an interface for communication with an imaging device which imaging device comprises a transmitter and a receiver, a user interface, and a processor, which processor is programmed to perform the following steps: inform the user, via the user interface, where to place the imaging device on a patient's body, instruct the imaging device to transmit radiation from the probe, receive reflected radiation from the imaging device, interpret the reflected information fully automatically using a learned algorithm, determine from the reflected radiation whether the imaging device is located correctly relative to a blood vessel of the patient, inform the user, if the imaging device is not located correctly, to reposition the imaging device and to repeat the instruct, receive and determine steps until the imaging device is correctly located, inform the user to apply pressure to the patient's blood vessel using the imaging device, instruct the imaging device to transmit further radiation, receive further reflected radiation from the imaging device, and determine from at least the reflected further radiation whether the blood vessel is obstructed. The system may be arranged to work with any other real-time imaging device by retraining and/or relabelling of new images. It may also work with other non-real-time methods, for example CT and MRI. For example, with a pressure cuff: scan uncompressed, scan under compression, evaluate difference. The problem may be simpler and the setup more expensive, but the same pipeline arrangement could still work. In relation to CT and MRI scans a skilled medical professional may still be required to be present doing the scan. The learned algorithm may comprise one or more elements of machine learning, and/or have been developed using machine learning.

Optionally, the reflected radiation and the further reflected radiation received from the imaging device comprise image data.

Image data is conventionally used as an output from many medical devices and can provide useful information regarding a patient.

Optionally, the processor is further programmed to instruct the imaging device to transmit and receive continuously. Optionally, the processor is further programmed to determine, from at least the further reflected radiation, whether the user is applying a predetermined pressure to the patient's blood vessel, and if this is not the case, to further inform the user to move the imaging device so as to adjust the pressure accordingly.

It can be advantageous for a user of the apparatus to be able to receive constant information regarding the patient and also whether the apparatus is being used effectively. This allows the user to make adjustments if necessary as well as providing clear information.

Optionally, the apparatus comprises an imaging device. Optionally, the imaging device is arranged to transmit ultrasound signals.

Such imaging devices can be inexpensive to produce, and readily available in a number of hospitals and related health clinics.

Optionally, the processor is programmed to determine whether the blood vessel is obstructed using one or more of: machine learning and/or deep learning algorithms.

Deep learning, which may be referred to as a specific technique within the broader term of machine learning, can be supervised, semi-supervised or unsupervised. Deep learning architectures can be applied to a broad range of fields, including medical image analysis, and generally learn through feature and/or representation allowing them to detect relevant information from raw data in an accurate and efficient manner.

Optionally, the processor is further programmed to provide an expert mode in which ultrasound images are provided directly to the user interface. Such a mode may be helpful for a skilled practitioner who does not require any feedback from the apparatus regarding its use.

According to a further aspect of the present invention, there is provided a computer-readable medium comprising instructions to be executed by processing logic for a device, having an imaging probe and a user interface, for diagnosing blood vessel obstruction, the instructions comprising the following steps: inform the user, via the user interface, where to place the imaging probe on a patient's body, instruct the probe to transmit radiation from the probe, receive reflected radiation from the probe, determine from the reflected radiation whether the probe is located correctly relative to a blood vessel of the patient, inform the user, if the imaging probe is not located correctly, to reposition the imaging probe and to repeat the instruct, receive and determine steps until the probe is correctly located, inform the user to apply pressure to the patient's blood vessel using the probe, instruct the probe to transmit further radiation, receive further reflected radiation from the probe, and determine from at least the reflected further radiation whether the blood vessel is obstructed.

According to a further aspect of the present invention, there is provided method of diagnosing blood vessel obstruction using an imaging probe and a computing device in communication with the imaging probe, which computing device comprises a user interface, the method comprising: informing a user where to place the imaging probe on a patient's body, transmitting radiation from the probe, receiving reflected radiation at the probe, determining from the reflected radiation whether the imaging probe is located correctly relative to a blood vessel of the patient, if the imaging probe is not located correctly, informing the user to reposition the imaging probe and repeating the transmitting and determining steps until the probe is correctly located, informing the user to apply pressure to the patient's blood vessel using the probe, transmitting further radiation from the probe, receiving further reflected radiation at the probe, and determining from at least the reflected further radiation whether the blood vessel is obstructed.

Optionally, the radiation transmitted from the probe is ultrasound radiation. Optionally, the radiation is transmitted continuously throughout the diagnosis. Optionally, the method of diagnosing blood vessel obstruction comprises a step of determining, from the reflected further radiation, whether the user is applying the correct pressure to the patient's blood vessel, and if this is not the case, repeating the pressure informing step prior to determining whether the blood vessel is obstructed.

The transmitted radiation may in in the form of acoustic radiation, specifically ultrasound, which utilises sound waves. These waves are in the form of pressure waves travelling through the medium to be analysed, and in this embodiment not electromagnetic waves. The term "energy" may be used interchangeably with radiation in relation to transmissions from the probe. the step for determining whether the blood vessel is obstructed is conducted by one or more of: machine learning and/or deep learning algorithms.

According to a further aspect of the present invention, there is provided a method of diagnosing blood vessel obstruction using an apparatus for diagnosing blood vessel obstruction, the method comprising: preparing a patient for the diagnosis, preparing a probe for the diagnosis, placing the probe on the patient at a location instructed by the apparatus, moving the probe on the patient as instructed by the apparatus, compressing a blood vessel of the patient as instructed by the apparatus, and obtaining from the apparatus an indication as to whether blood vessel obstruction is suspected.

Optionally, Doppler Imaging can be used along with the above aspects in order to determine the blood flow speed as well as direction of blood flow. Using a combination of B-Mode imaging and Doppler techniques can increase the accuracy of some or all aspects described.

BRIEF DESCRIPTION OF THE DRAWINGS

Embodiments will now be described, by way of example only and with reference to the accompanying drawings having like-reference numerals, in which:

FIG. 1 illustrates an ultrasound probe coupled to a computing device;

SPECIFIC DESCRIPTION

Embodiments of the invention mainly comprise two parts, an ultrasound probe 100 and a computing device 101 having a user interface shown, for example in FIG. 1.

The ultrasound probe 100 operates in a conventional manner, i.e. it transmits ultrasound radiation and receives ultrasound radiation reflected by the tissues of a patient. Many ultrasound probes are suitable for use with embodiments of the invention provided that they have a suitable form factor (i.e. are small enough to be placed correctly against the patient's body) and have sufficient power and sensitivity (i.e. can transmit ultrasound deeply enough into the patient's tissues and detect the reflected ultrasound radiation). A suitable ultrasound probe 100 is the Philips Lumify™ portable ultrasound probe that conveniently includes a USB interface for connection to a computing device such as a smartphone or tablet (not shown). A Clarius™ probe may also be used and connected to computing device through an Internet connection, such as WiFi. Note that other computing devices 101 are also suitable for practising the present invention, that the probe and the computing device could communicate other than via a wired connection (e.g. wirelessly) or could even be combined into a single unit.

Figure 2:
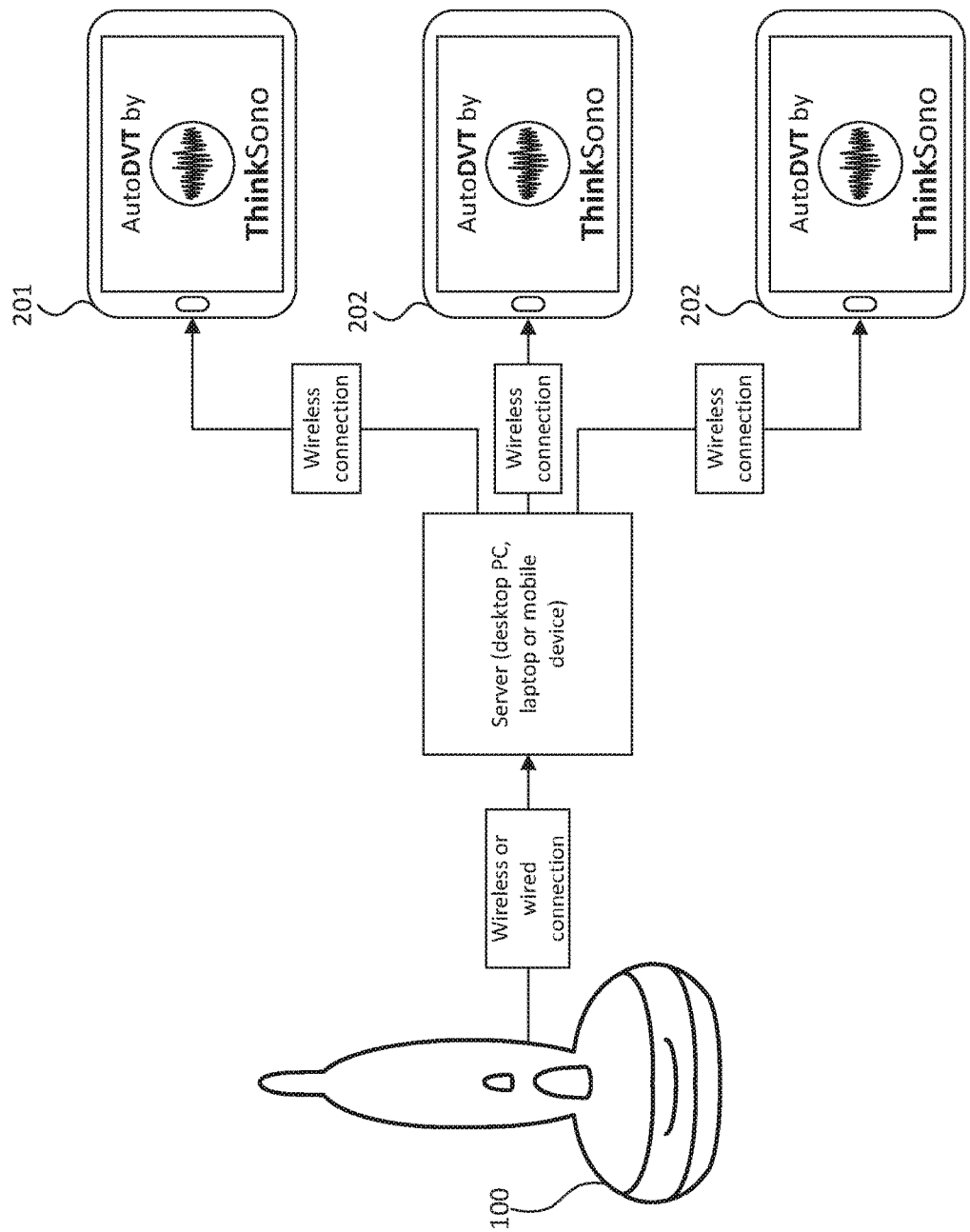
FIG. 2 illustrates a schematic for the use of the system in server-multi-client mode.

Machine learning algorithms and models can be executed on single (e.g. mobile) computing devices or in a server-client mode. The latter is depicted in FIG. 2. In the server-client mode a constant stream of images is streamed to a computing device acting as server. The server processes the images, evaluates if the relevant vessel is visible, if a landmark has been found and/or if the vessel is compressible in real-time. This information is forwarded to light-weight client computing devices, e.g. tablet computers or mobile phones that have established a private data connection, e.g. through WFi, to the server. The data may be displayed in a light-weight, e.g. browser-based, user-interfaces 201, 202. A user may be able to connect more than one user interface devices for example for training or monitoring purposes. In such an embodiment, one or more observing users 202 may take their display from the main user 201.

Machine learning is the field of study where a computer or computers learn to perform classes of tasks using the feedback generated from the experience or data gathered that the machine learning process acquires during computer performance of those tasks.

Typically, machine learning can be broadly classed as supervised and unsupervised approaches, although there are particular approaches such as reinforcement learning and semi-supervised learning which have special rules, techniques and/or approaches. Supervised machine learning is concerned with a computer learning one or more rules or functions to map between example inputs and desired outputs as predetermined by an operator or programmer, usually where a data set containing the inputs is labelled.

Unsupervised learning is concerned with determining a structure for input data, for example when performing pattern recognition, and typically uses unlabelled data sets. Reinforcement learning is concerned with enabling a computer or computers to interact with a dynamic environment, for example when playing a game or driving a vehicle.

Various hybrids of these categories are possible, such as "semi-supervised" machine learning where a training data set has only been partially labelled. For unsupervised machine learning, there is a range of possible applications such as, for example, the application of computer vision techniques to image processing or video enhancement. Unsupervised machine learning is typically applied to solve problems where an unknown data structure might be present in the data. As the data is unlabelled, the machine learning process is required to operate to identify implicit relationships between the data for example by deriving a clustering metric based on internally derived information. For example, an unsupervised learning technique can be used to reduce the dimensionality of a data set and attempt to identify and model relationships between clusters in the data set, and can for example generate measures of cluster membership or identify hubs or nodes in or between clusters (for example using a technique referred to as weighted correlation network analysis, which can be applied to high-dimensional data sets, or using k-means clustering to cluster data by a measure of the Euclidean distance between each datum).

Semi-supervised learning is typically applied to solve problems where there is a partially labelled data set, for example where only a subset of the data is labelled. Semi-supervised machine learning makes use of externally provided labels and objective functions as well as any implicit data relationships. When initially configuring a machine learning system, particularly when using a supervised machine learning approach, the machine learning algorithm can be provided with some training data or a set of training examples, in which each example is typically a pair of an input signal/vector and a desired output value, label (or classification) or signal. The machine learning algorithm analyses the training data and produces a generalised function that can be used with unseen data sets to produce desired output values or signals for the unseen input vectors/signals. The user needs to decide what type of data is to be used as the training data, and to prepare a representative real-world set of data. The user must however take care to ensure that the training data contains enough information to accurately predict desired output values without providing too many features (which can result in too many dimensions being considered by the machine learning process during training, and could also mean that the machine learning process does not converge to good solutions for all or specific examples). The user must also determine the desired structure of the learned or generalised function, for example whether to use support vector machines or decision trees.

The use of unsupervised or semi-supervised machine learning approaches are sometimes used when labelled data is not readily available, or where the system generates new labelled data from unknown data given some initial seed labels.

Machine learning may be performed through the use of one or more of: a non-linear hierarchical algorithm; neural network; convolutional neural network; recurrent neural network; long short-term memory network; multi-dimensional convolutional network; a memory network; or a gated recurrent network allows a flexible approach when generating the predicted block of visual data. The use of an algorithm with a memory unit such as a long short-term memory network (LSTM), a memory network or a gated recurrent network can keep the state of the predicted blocks from motion compensation processes performed on the same original input frame. The use of these networks can improve computational efficiency and also improve temporal consistency in the motion compensation process across a number of frames, as the algorithm maintains some sort of state or memory of the changes in motion. This can additionally result in a reduction of error rates.

Figure 3:
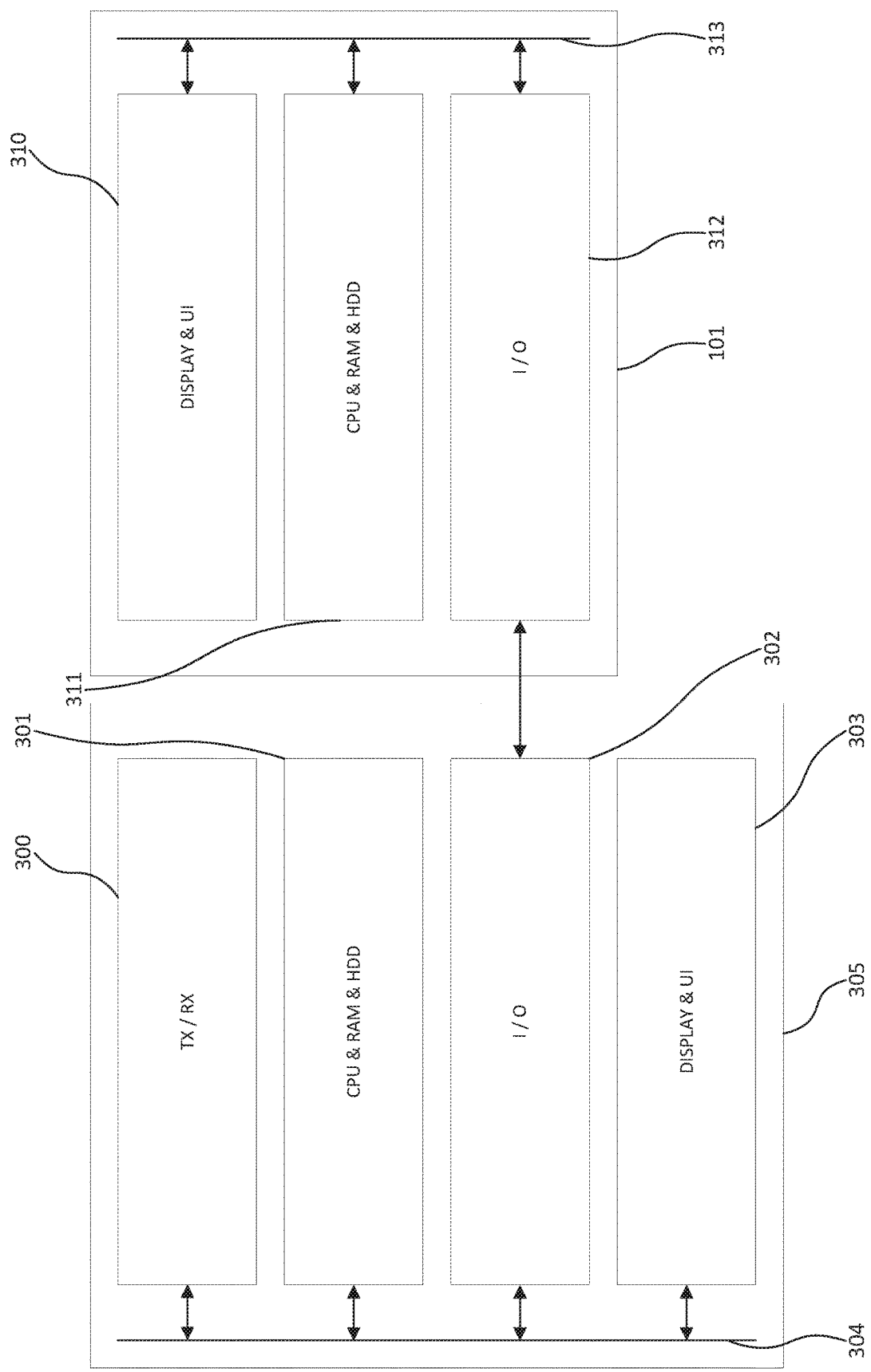
FIG. 3 illustrates an overview of the system.

FIG. 3 shows a high-level block diagram of an image acquisition system/device 305, optionally a probe, and computing device 101. The image acquisition device 305 comprises a transmitter (TX) and receiver (RX) 300 which may transmit and receive ultrasound radiation, a processor 301 comprising a processing unit and a memory, optionally wherein the processing unit is a central processing unit (CPU) and optionally wherein the memory is a random access memory (RAM), optionally wherein the processor 301 comprises a hard disk drive (HDD) and/or a graphics processing unit (GPU). The components of the image acquisition system/device may communicate via a data bus 304. Optionally, the image acquisition system/device also comprises a display and user interface component 303. The image acquisition system/device 305 operates under the control of software in the computing device to transmit ultrasound radiation into a patient and to return the reflected signals to the computing device 101 through an input device and an output device 302 (such as a touch-screen). The reflected signals to the computing device 101 may optionally be through a user interface 303 comprising an input and output device 302. Within the computing device 101 there are an interface 310, a processor and memory 311, and a user interface comprising an input device and an output device 310 (such as a touch-screen). The components of the computing device may communicate via a data bus 313. The image acquisition system/device 305 and computing device 101 communicate via their respective input/output hardware 312, 302 which can for example be via a USB connection, other wired connection, via Bluetooth, and/or other wired or wireless connection.

To facilitate the above, the following outlines an approach to make sure that each acquired frame is processed, robust input/output (I/O) communication between ultrasound probe 100 and computing devices 101 may be ensured through a multi-buffer asynchronous communication system. The architecture 400 of the prediction device software layer is outlined in FIG. 4. This ensure real-time performance frames are processed in a first-in-first-out (FIFO) fashion. If, due to unforeseen circumstances, (e.g. operating system caused) drops in processing power occur the proposed approach will drop frames to maintain real-time performance and instruct the user.

Figure 4:
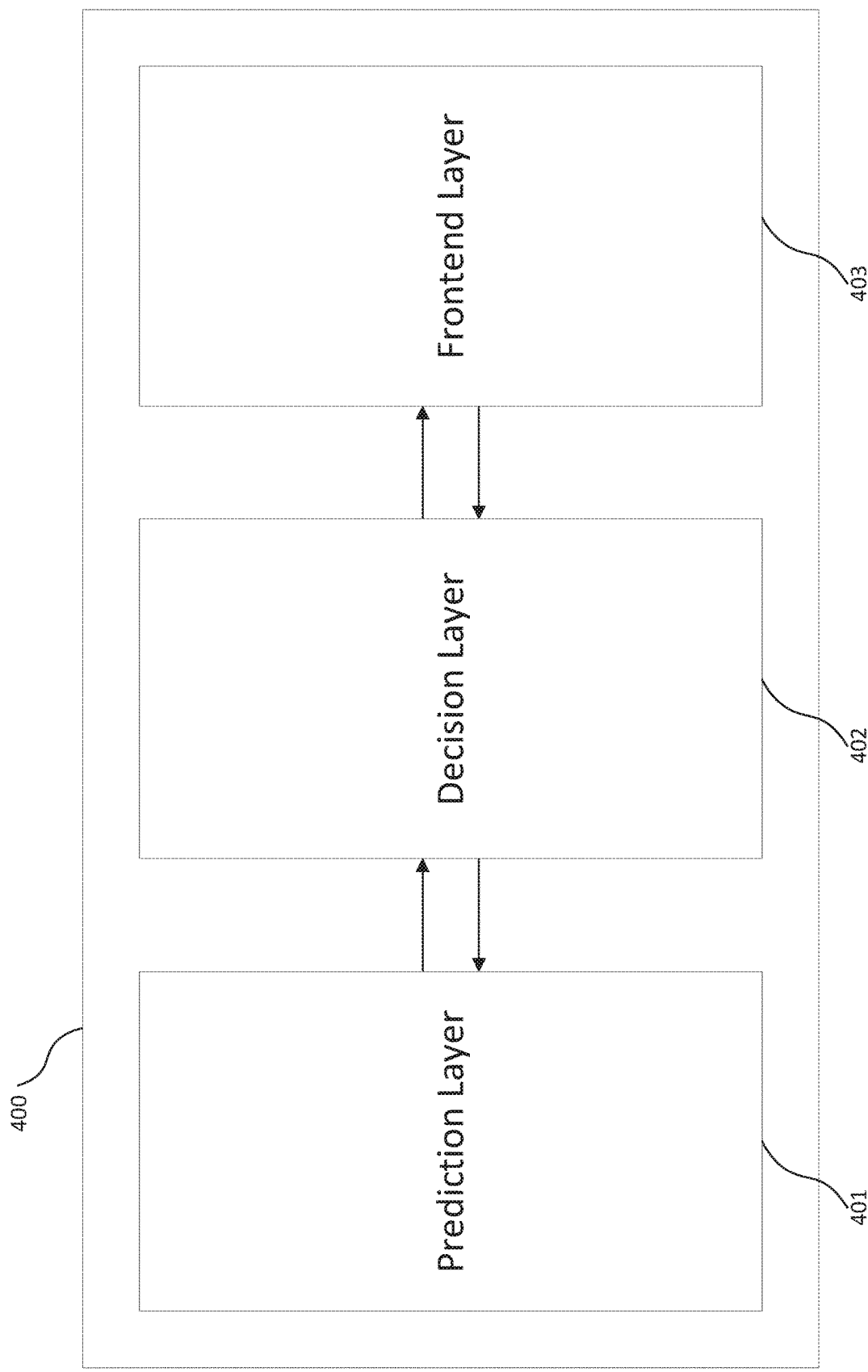
FIG. 4 illustrates an exemplary high-level software layer architecture overview.

In order to break down the complexity of diagnosis and guidance, the software is designed in layers as shown in FIG. 4. These layers comprise a Prediction layer 401, a Decision layer 402, and a Frontend layer 403. Each layer only communicates with its neighbouring layers, similar to the TCP/IP stack. The different tasks of image acquisition, image analysis, diagnosis decision as well as GUI and user instructions are decoupled from each other in the different layers. The purpose of the Prediction, Decision and Frontend Layers is outlined in FIG. 5.

The software part of the system is a multi-threaded application aiming to provide real-time analysis of the input ultrasound image stream. Each layer is made up of components, buffers, items and event loops. Each component is a thread on its own, representing a processing unit for incoming images or event. Buffers are thread safe worker queues to share processed data between components. The shared data in the buffers is wrapped into queue items. Event loops are used to communicate asynchronously between components.

Figure 5:
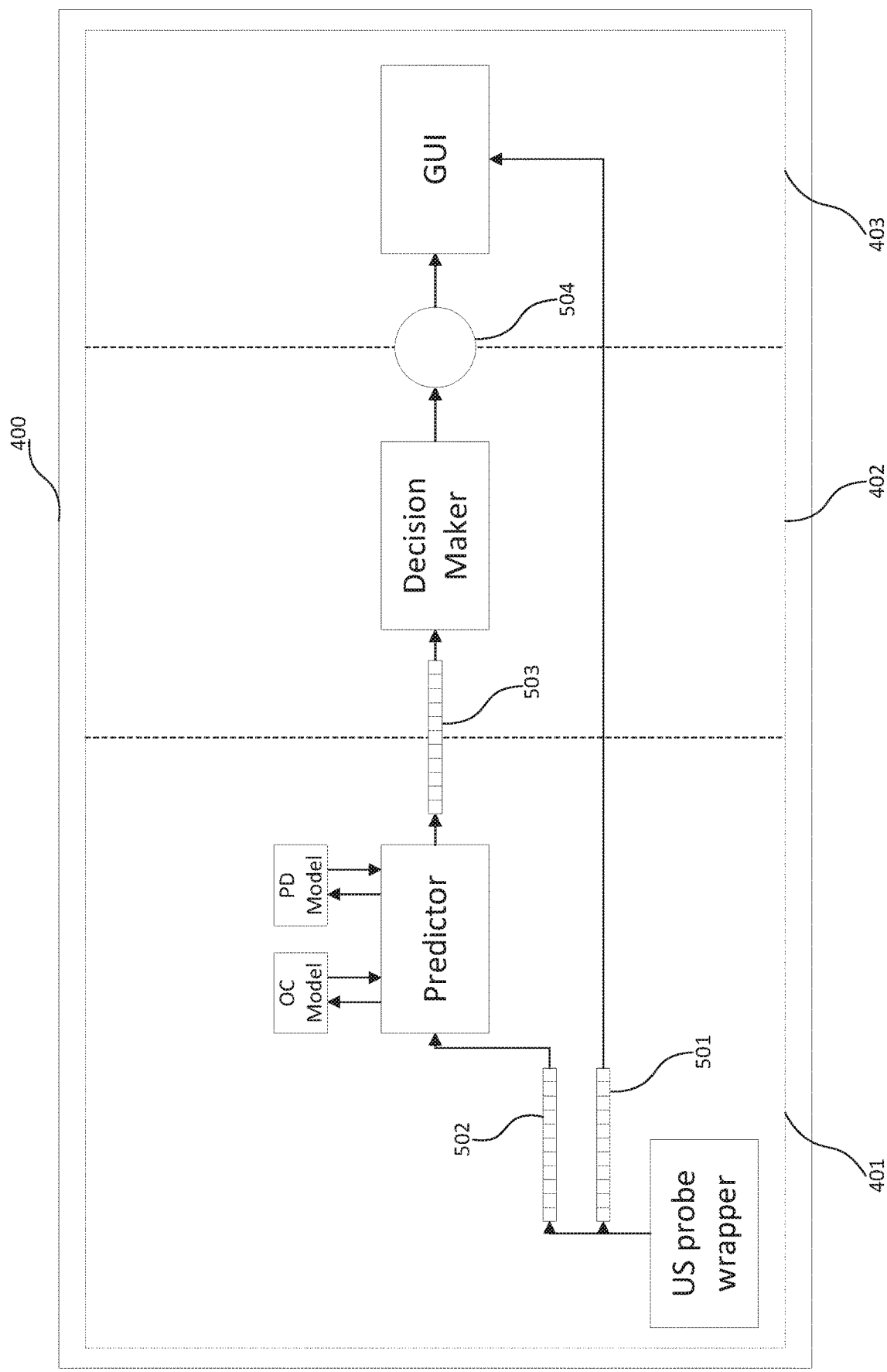
FIG. 5 illustrates a detailed overview over multi-stage buffer system to guarantee real-time performance.

The system as disclosed in FIG. 5 is divided into three main parts:

(1) The Prediction Layer 401 is the most low-level layer. This layer acquires images from an image stream pushed from a handheld ultrasound probe, e.g. Clarius™, and then analyses the image content with the DVT-related machine learning models in a predictor module. These models may comprise opened/closed state detection ("OC") and/or plane detection ("PD") models carrying out predictions asynchronously. State detection of the vessel may take place after pressure is applied. The PD model may alternatively or in addition comprise landmark detection and/or anatomical reference plane detection. Frontend frames may be queued in the Frontend frame queue 501, before being pulled to the graphical user interface (GUI). Other frames may be queued in the frame queue 502 before being pulled to the predictor module. The images are read consistently at a stable FPS from the probe. Once an image is transferred from the probe to the Prediction Layer the image is run through adequate machine learning models in real-time. The prediction output as well as the original input image are provided for the next layer in the form of a predicted frame queue 503. The predicted frame queue 503 is pushed from the predictor module and pulled to the decision maker module.

(2) The Decision Layer 402 provides the diagnosis decision logic for the presented system within the decision maker module. It takes the analysed output of the image stream. The layer validates if the current sequence is a clinically relevant for the DVT diagnosis exam. It decides if a clot is present in the current sequence. If the current sequence of images represents a faulty executed exam, it decides that the exam has to be repeated. All these decisions encapsulate the instructions given to the operator to carry out a valid exam and if carried out correctly, the final status of the diagnosis. These decisions are modelled as a state machine. Every time a decision is made the Frontend Layer is notified through one or more messages transmitted through a dispatcher module 504. The Frontend and/or the GUI itself is operable to detect messages.

(3) The Frontend Layer 403 is the top-most layer. It contains the graphical user interface. The GUI visualizes the decisions and input of the decision layer. It reacts accordingly every time a new decision is made. This layer takes operator configuration input, e.g. which leg is examined. These configurations are propagated back into the Decision and Prediction Layers.

The computing device 101 is arranged to provide the appropriate instructions for driving the ultrasound device 100, to instruct a user (who typically will not be an ultrasound imaging specialist or radiologist) how to place the probe 100 on a patient and to interpret the reflected signals. Interpreting the signals to ensure that the probe 100 is correctly placed and to determine whether the patient is at risk of a blood clot, for example DVT, may involve the following parts:

(1) A constant stream of images, transferred from the probe, is automatically and in real-time classified into images containing the correct vessel in the designated scan area or not. This is achieved using machine learning techniques (convolutional neural network) that have been trained on a large number (conventionally >100) of correctly acquired DVT examinations. The user is instructed to move the probe in the defined region of interest if no vessel is identified, until the relevant vessel is central in the field of view of the probe. The system provides feedback to the user as soon as the currently acquired image contains the desired vessel and instructs the user to keep this position. The image stream is constantly monitored throughout (2) if an image of the correct vessel is acquired or if the user moved out of the desired imaging area.

(2) Being above the right vessel simplifies guidance to one degree of freedom. If a correct vessel is identified, the system instructs the user to move along this vessel, i.e., 'up' or 'down' (e.g., towards genital area or knee in case of groin area examination) until the first of a predefined number of landmarks is identified. The identification of landmarks is based on machine learning (convolutional neural network) and has been trained on previous DVT examinations. As soon as the starting landmark has been found the system notifies the user and instructs to apply pressure while evaluating (3). If (3) is successful, the system instructs the user to move 'down' (e.g. towards the knee in case of groin measurements) along the vessel until the next landmark is automatically identified. (3) is evaluated at each of a number (2-8) of pre-defined landmarks.

(3) If (1) and (2) are fulfilled, i.e., the system is certain that a relevant vessel is examined (1) and that the probe location corresponds to standard DVT examination protocol landmarks, the user is instructed to apply pressure with the probe. The resulting image stream is automatically evaluated using machine learning models (convolutional neural network) that have been trained on data from DVT examinations. If the system robustly, i.e. for more than a defined number of frames, identifies the vessel as compressed a positive feedback is given to the user and is instructed to move further 'down' to the next landmark until all landmarks have been identified as compressible vessels. If one of the landmarks is not identified as compressible the patient is referred to further examination by an expert.

Guidance does not necessarily require external tracking for the presented approach. The guidance information is automatically derived from the image information only and previously trained machine learning examination models. If the probe moves too far out of the region of interest and the vessel is not contained in the image stream, the user is instructed to start at part (1) and to process back to the starting landmark of the examination protocol. In this embodiment, all pre-defined landmarks must fulfil part (3) to yield a negative diagnostic for DVT, and all decisions are filtered to provide temporal consistency. This may be achieved through Kalman filtering and Long short-term memory units.

The software for the computing device 101 may be pre-installed on the device, downloaded from a remote server (such as from an app store) or loaded from local storage such as an optical disk.

While the following example refers to deep vein thrombosis (DVT) the skilled person will appreciate that the technique can be applied to other medical imaging tasks and/or vessel related assessments such as: detecting abdominal aortic aneurysm; carotid artery stenosis; kidney stones; gallstones; testicular torsion; other forms of atherosclerosis; and/or other applications within the field of Nephrology such as assessment of fistulas.

In some embodiments the computing device 101, under the control of the software, has to provide a hardware controller to control the ultrasound probe 100 appropriately. In other embodiments, the computing device 101 merely interacts with the probe 100 to cause the probe 100 to operate in the way required by the use of the device 101. The system may provide pre-defined optimal settings for a number of probes and regions of interest. Optionally, ultrasound probe-specific settings are automatically provided to adjust the used ultrasound probe for the instructed examination protocol.

Additionally, the ultrasound probe 100 will usually provide an interface which is used to control depth, gain, focus and zoom. These terms are well known as are the appropriate settings therefor to detect DVT. Image can be automatically adjusted once data is being fed into system, but alternatively can get user to do this. Some models of ultrasound probe 100 may be capable of a degree of automatic configuration. In some embodiments the computing device 101 further comprises an interface to receive the ultrasound signals/data from the probe 100.

The computing device 101 further has to provide computer vision and analysis of the images generated by the ultrasound probe.

Once the computing device has received the reflected images, an additional task of automated vessel segmentation is carried out. This is achieved in real-time using machine learning models (convolutional neural U-net) trained on pixel-wise expert annotations of a number of (conventionally >100) DVT examinations. In one embodiment, the result of the segmentation is provided, via the user interface, to the user in a high-level abstracted form. This form can be deformable circles, representing the vessel walls, arranged according to the anatomical situation at the currently examined landmark. The interpretation of "raw" ultrasound images conventionally requires an expert so the user is provided with a simplified view showing only the vein or veins of interest, thus simplifying the user's task. Current deformation state is translated to deformation of the presented circles in the user-interface. The field of view is represented as simple box and the circles position relative to the box represent the vessel's real position relative to the frame of the ultrasound image. This provides feedback to the user to keep the vessel centred and not to move the vessel out of the field-of-view required for vessel-centred guidance. An example is shown in FIG. 3. Such a view will be further discussed below with reference to FIGS. 9 to 13.

Figure 6:
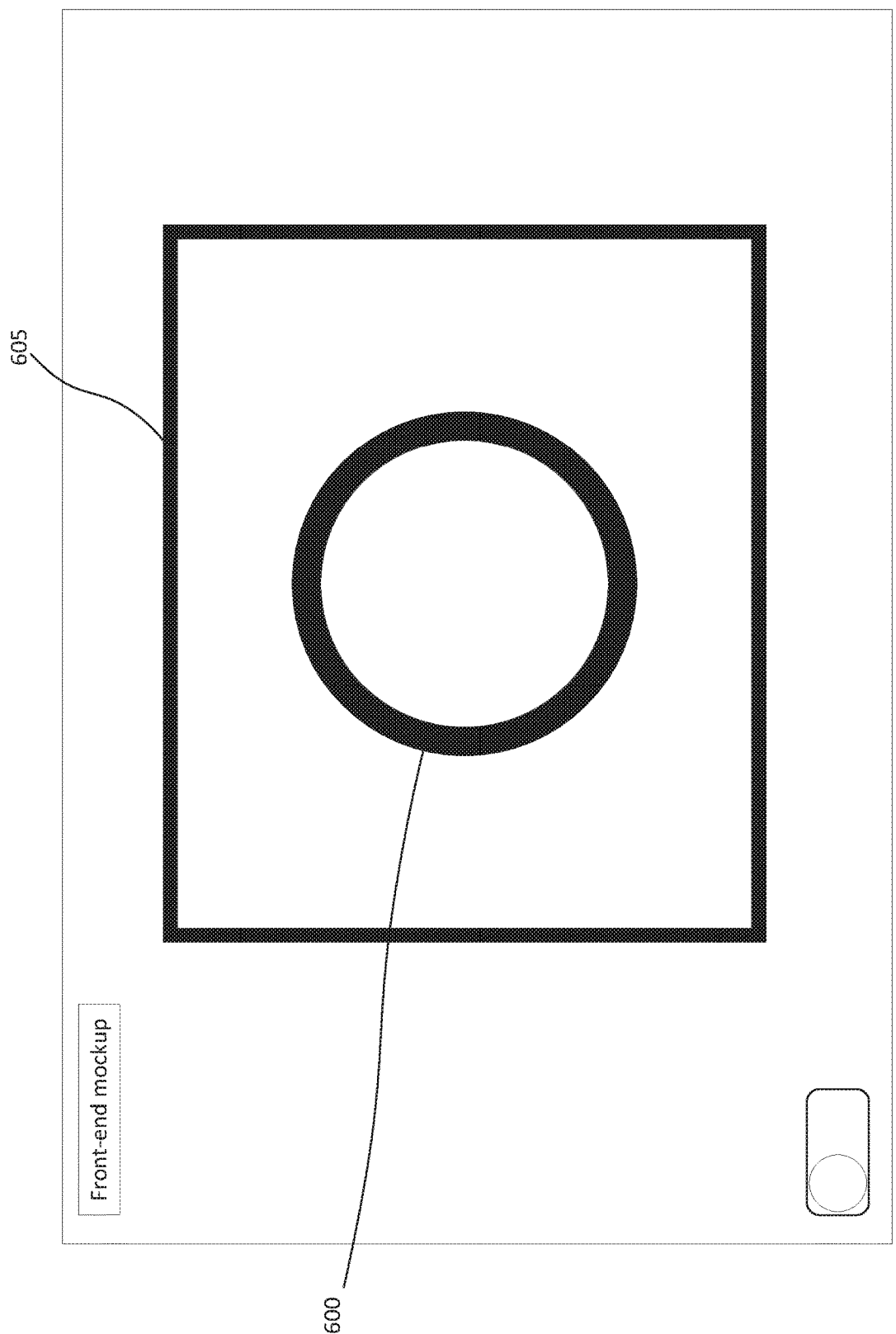
FIG. 6 illustrates an abstract vessel representation surrounded by a maximum movement perimeter.

Referring to FIG. 6, the circle 600 represents an abstract vessel representation and the surrounding black box 605 represents a maximum movement perimeter. If the circle 600 is outside the black box 605 then the protocol may be reset. Looking at a sequence of segmented vessels the system can reconstruct a 3D model of the vein in real-time. This model can be used together with the vessel boundaries, open-closed state, DVT prediction, pressure, angle and body part information to generate a feedback loop for the user. Therefore every time new image information is available (usually at about 20 frames per second), new information is available to the system to reassure or correct the user during the exam.

The above tasks are performed in at least some embodiments using learned approaches, including machine learning and/or deep learning. In this embodiment, a deep learning approach is adopted, utilising one or more Deep Learning algorithms. Each of these deep learning tasks will run in real-time on the computing device. Deep learning is a subfield of machine learning based on algorithms inspired by the human brain and using software-implemented neural networks. The one or more algorithms make predictions and perform image analysis based on labelled datasets. The algorithms used may include convolutional neural networks, U-Nets with skip connections, and/or long short-term memory (LSTM) algorithms. There is also an option to determine one or more learned approaches with heuristics based on a robust segmentation. In one embodiment, a deep learning network is used to derive this information from the images directly, however, it would also be possible to use for example a segmentation network (or any other robust segmentation approach) to generate a good segmentation and the implement the program logic manually (e.g. count the number of lumen voxels until they are less than a certain threshold then a vessel is compressible).

Each of these deep learning tasks requires a labelled dataset. The labelled dataset is a set of ultrasound images showing DVT exams in which the blood vessels are marked explicitly. It is possible to use the same raw ultrasound images for several of these tasks, but a unique set of labels for each task is provided in this embodiment. Labelling data is a time-consuming matter that also requires medical knowledge to verify the accuracy of the labels. In the end, inaccurate labels will cause inaccurate predictions. A certain percentage of inaccurate labels (conventionally between 1-10%) is acceptable for deep learning methods because the learned models adopt to the most prevalent and important features in a general way. Outliers are not a significant problem in such approaches but can be mitigated by manual data sanitation and model validation by experts. For the latter, an interface is available that shows the raw ultrasound images together with the computed label, decision criteria and segmentations.

Finally, the algorithm running on the computing device provides a user interface to instruct the user what to do. Images from a suitable graphical user interface are discussed below with reference to FIGS. 9 to 13 and the skilled person will readily know how to implement a suitable interface.

The algorithm running on the computing device 101 may further be arranged to provide the following enhancements.

It is possible to execute and train machine learning algorithms for the tasks of vessel guidance, landmark verification, and compressibility state identification individually or to combine all tasks in a single network architecture and train all tasks at once, so called end-to-end training. The disclosed system allows both approaches. Individual models and the combined model achieve the same accuracy for the individual tasks. However, a combined, end-to-end trained machine learning model requires less latent parameters and less computational resources than individual task-processing. The end-to-end machine learning method can be compressed to a small size so that it is significantly faster than individual models, requires less memory and is computationally light-weight for real-time processing with at least 20 frames per second on mobile computing devices.

Determining whether there is enough gel on the probe. Since the ultrasound image quality deteriorates when there is inadequate gel to couple the ultrasound radiation to/from the patient's tissues, the system is preferably arranged to inform the user to re-apply gel to the probe (or patient) as appropriate. The algorithm can warn the user, since the image data is deteriorating, that more gel is required on the probe.

To determine physically whether there is a blood clot in a patient, compression of the veins in a systematic way is required. Relative pressure can be deduced from the change in image sequences when instructing a user to perform the physical compression step for each portion of a patient vein being tested. This is useful to indicate to a user that too much or too little pressure is being applied during the compression phase, for example it is undesirable to bruise the patient. If the vein does not compress this can mean that there is too little pressure or DVT. If the vein does not compress the system will instruct to keep trying. If compression cannot be achieved despite pressing in a reasonable way, it is the operator's decision to stop at this point and to refer to an expert.

From the nature of the reflected images, the algorithm can determine the angle at which the probe has been applied to the patient. Typically, the user should hold the probe perpendicular to the patient's skin and, if this is not the case, the user may be advised to rectify this.

The algorithm may further provide registration to a body part. What this means is that the current location of the probe (knee, thigh etc.) can be determined automatically. Typically this is done by identifying the so-called "landmarks" that a radiologist would use at the commencement of an examination. There is a high prevalence of a patient having DVT in these landmarks. Thus the nature of the particular test can be stored together with the relevant results. This saves the user, for example, having to identify manually to the software exactly where the probe is at any point during the physical examination or when a data point of interest is collected by the probe.

The software may further be provided with an introduction to the diagnostic procedure to be conducted—this could be a short video that the user can show to the patient.

It may be further provided with a "walk-through" of the procedure for the user—again this can be a short video to teach or remind the user what he or she is about to do and can be skipped if not required.

The actual process instructed by the software and conducted by the user will now be described.

Figure 7:
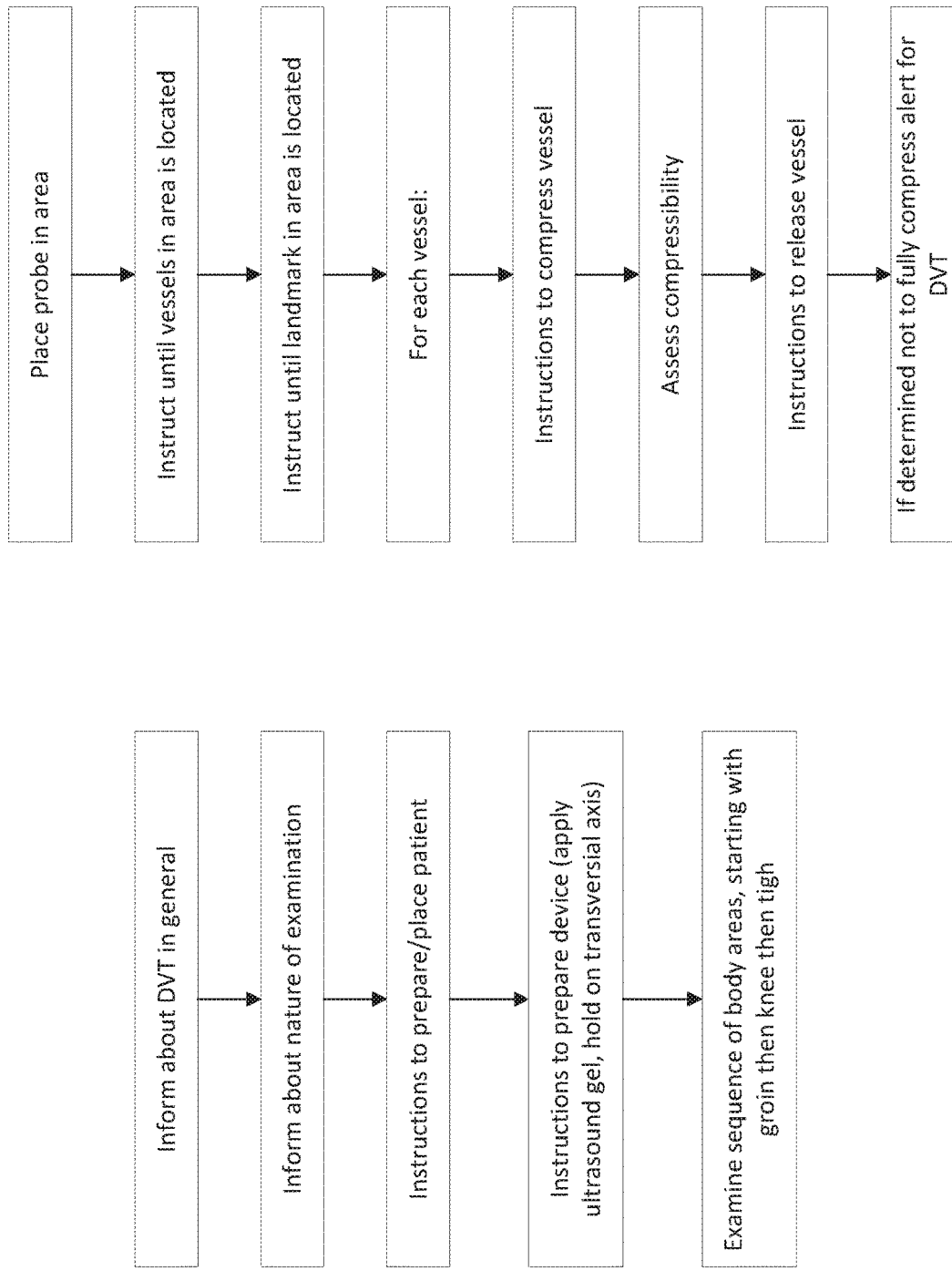
FIG. 7 illustrates a set of steps to be performed by a user according to an embodiment.

FIG. 7 illustrates a set of steps to be performed by a user according to an embodiment. These steps may be provided to a user in order to allow them to operate the apparatus effectively.

Figure 8:
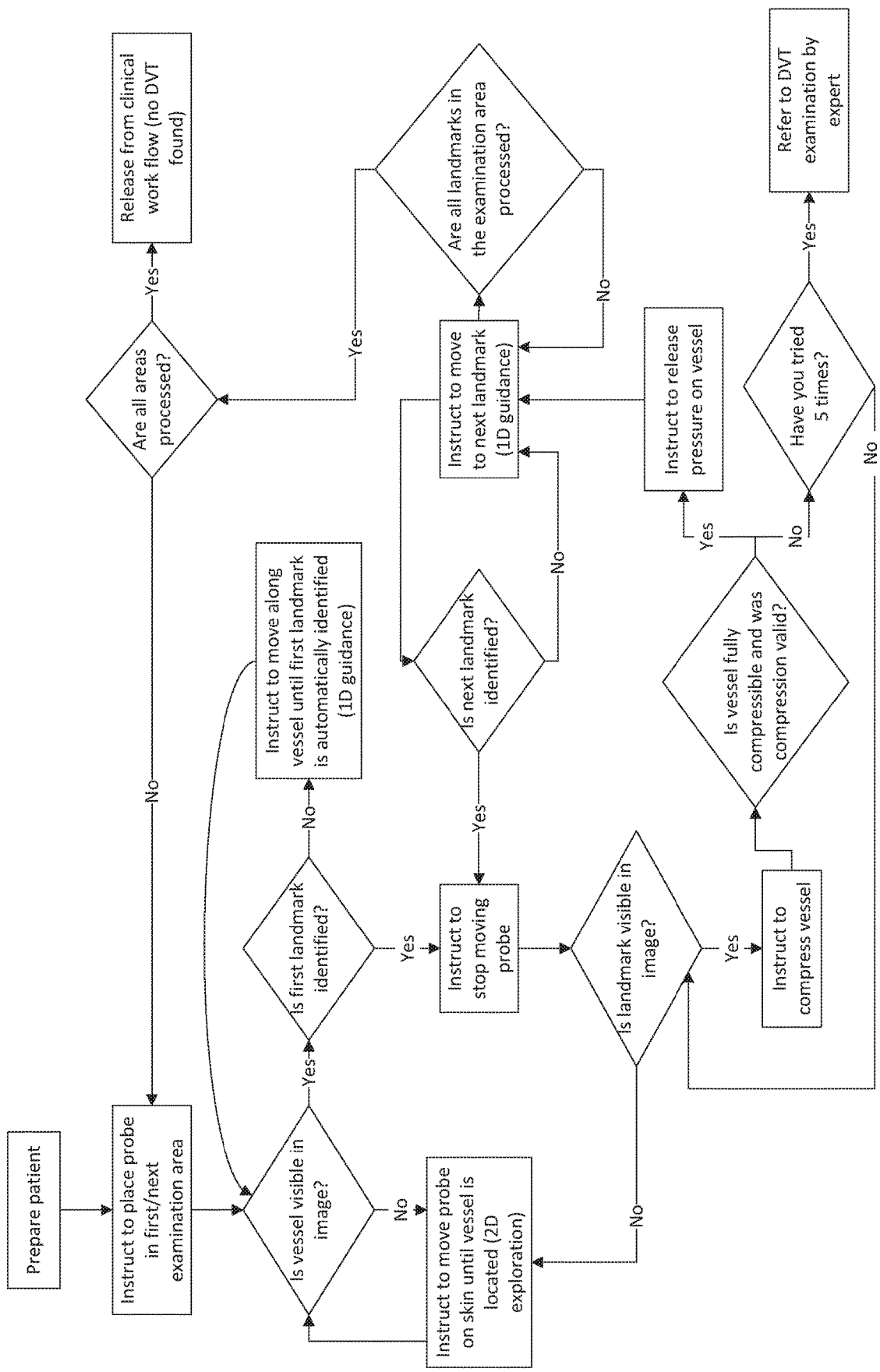
FIG. 8 illustrates a typical workflow for DVT examination.

FIG. 8 illustrates a typical workflow for DVT examination. After the patient has been prepared the system instructs the user to place the probe in a defined examination area. The user explores the area until the system automatically detects the relevant vessel. It is permanently evaluated during the examination if the correct vessel is visible. If the vessel is identified the user is instructed to move along the vessel until landmark 1 is reached. Feedback is provided through an interface similar to that shown in FIG. 6. If a landmark is automatically identified the user is instructed to compress the vessel. If the method identifies the vessel to be compressible at the landmark position, and that the compression itself was validly performed, it instructs the user to move to the next landmark until the examination area is finished and all defined landmarks have been processed. If the vessel is not compressible at a certain landmark and/or the compression itself was not validly performed, the user is questioned as to whether they have tried this process five times already. The number of attempts may be varied, but in this embodiment is set as five. If after these five attempts the vessel is still not compressible at a certain landmark and/or the compression itself was not validly performed, the patient is referred to a specialist. If the probe is moved outside of the examination area the user is instructed to start over for this vessel at the first landmark. If all landmarks in all examination areas are automatically identified to be compressible, the patient is discharged from the clinical work flow.

Figure 9:
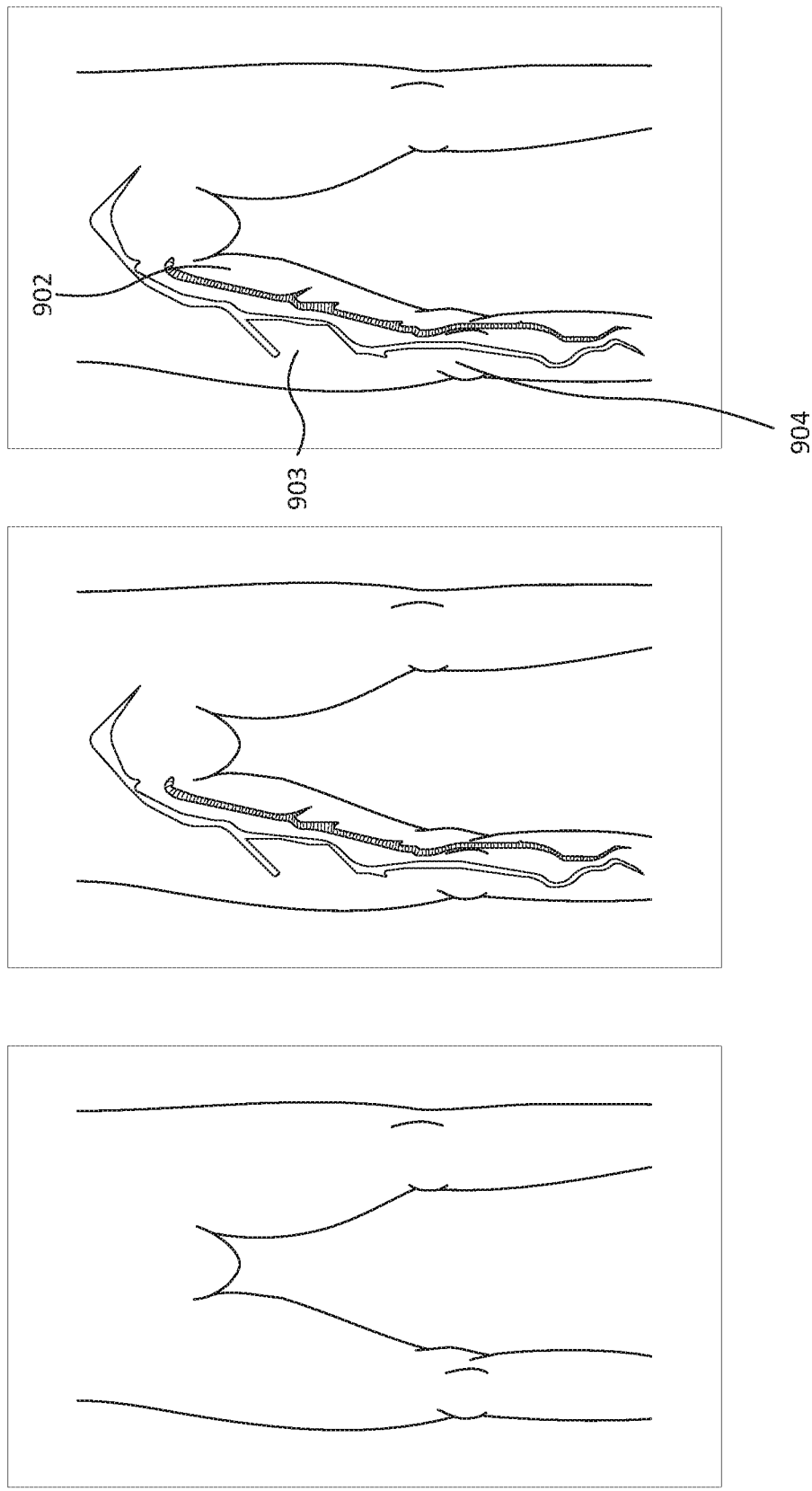
FIGS. 9 to 13 illustrate a sequence of example UI images to be conducted during the patient testing.
Figure 10:
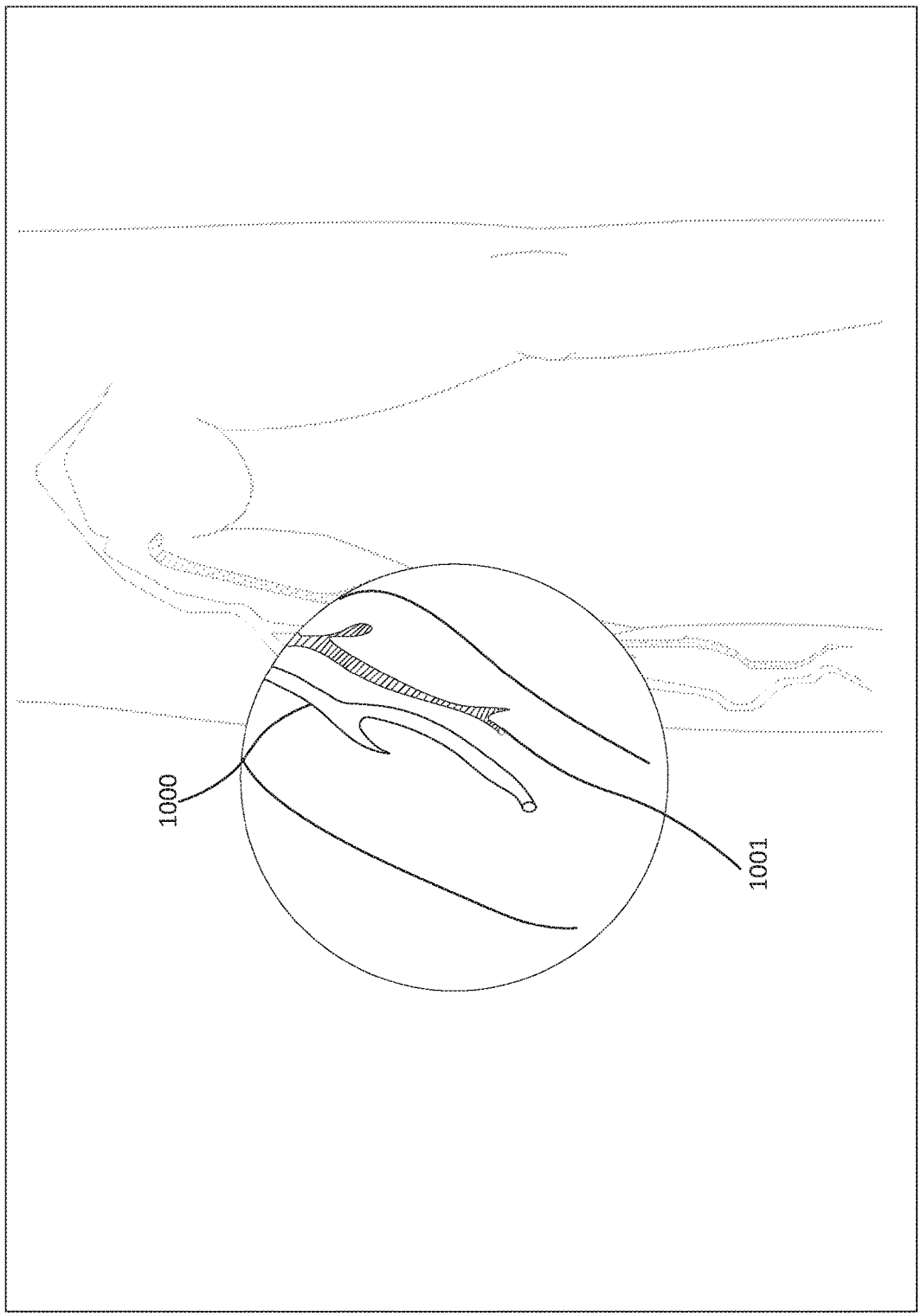

FIG. 9 shows the legs of a patient 900 including the three main areas in which the examination conventionally takes place: the groin 902, thigh 903, and knee 904. FIG. 10 shows a simplified view of the veins of interest in a DVT examination 1000 and 1001.

Figure 11:
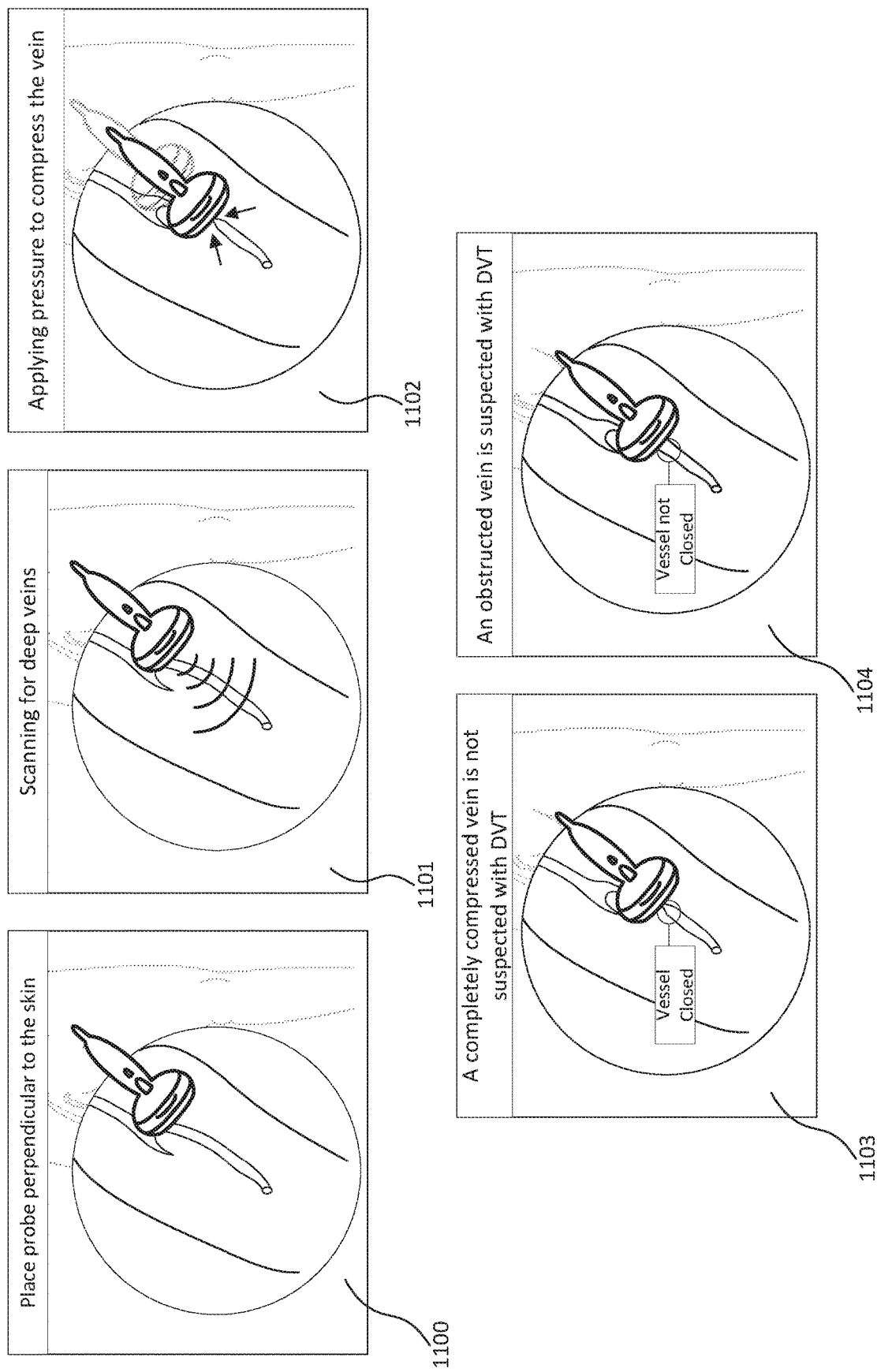

FIG. 11, feature 1100 illustrates the placing of the probe perpendicular to the patient's skin, starting in the groin area of the patient's right leg. The system then interprets the returned ultrasound data as discussed above to instruct the user in the placement of the probe until the blood vessels are located as in FIG. 11, feature 1101. This can conveniently be done via the graphical user interface on the computing device. In addition to informing the user of the correct location, the system can also notify the user whether the probe is not perpendicular.

Figure 13:
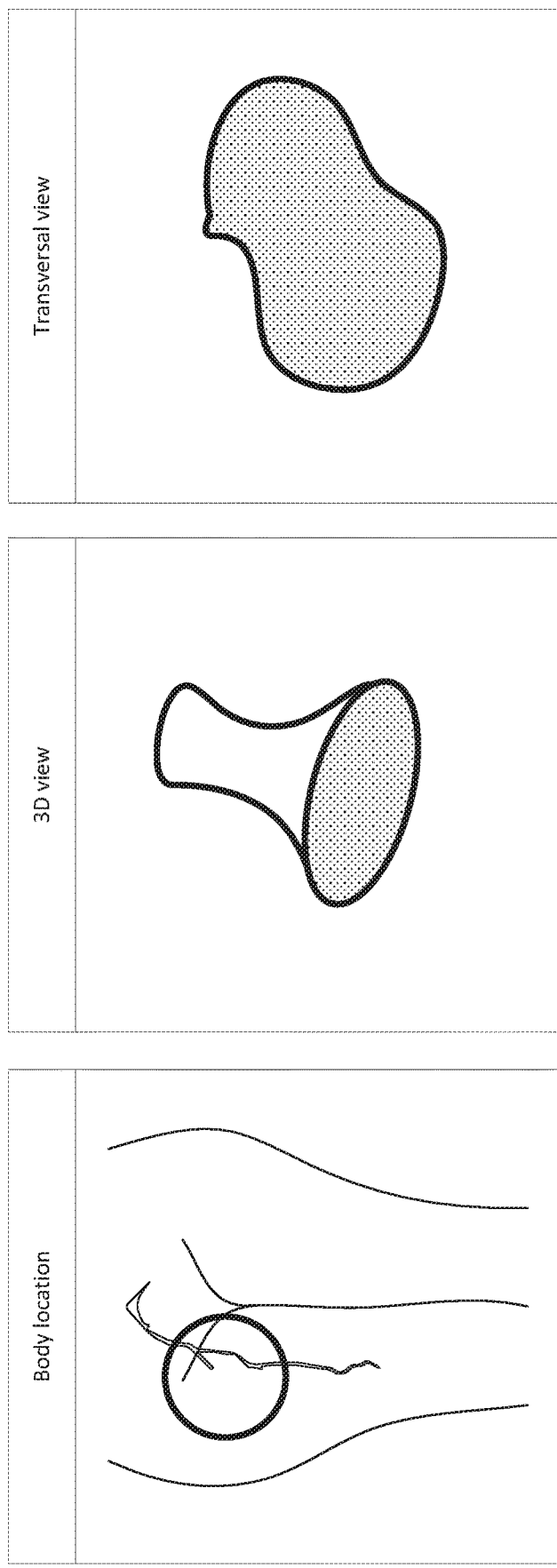

Once the blood vessels are located the system instructs the user in the placement of the probe until the landmark in the groin is located. This is repeated until a suitable 3-D map of the blood vessels in the groin has been generated. FIG. 13 shows an expanded, simplified view of two such blood vessels.

The system now determines which veins to test for DVT and instructs the user to compress a blood vessel as in FIG. 11, 1102 and shows a still further simplified view in which only the vein of interest is shown. The user is instructed to compress the vein as shown in FIG. 11, 1102 and the system assesses the compressibility.

FIG. 11, feature 1103 shows a vein that is closed successfully by the application of the pressure while FIG. 11, feature 1104 shows a vein that is not closed successfully and is suspected of DVT.

FIG. 11 shows a possible view shown to a user in which the Body Location view shows a miniature model of the body showing the approximate location of the probe. The 3D view shows a larger model of the currently-assessed vessel segment while the transversal view shows a cross-cut of the vein. All of these views update in real time as the probe is moved or the vessel squeezed.

The system then instructs the user to release a blood vessel and, if it was determined that there is a risk of DVT, it alerts the user. The sequence is repeated for further veins/areas and legs of the patient. The system may be arranged to tell the user that the vessel is definitely compressible, i.e. definitely no DVT is present. If it is not compressible there might be also other reasons and referral to an expert radiologist is required. The system will keep instructing to compress the current landmark until the operator gives up.

Figure 12:
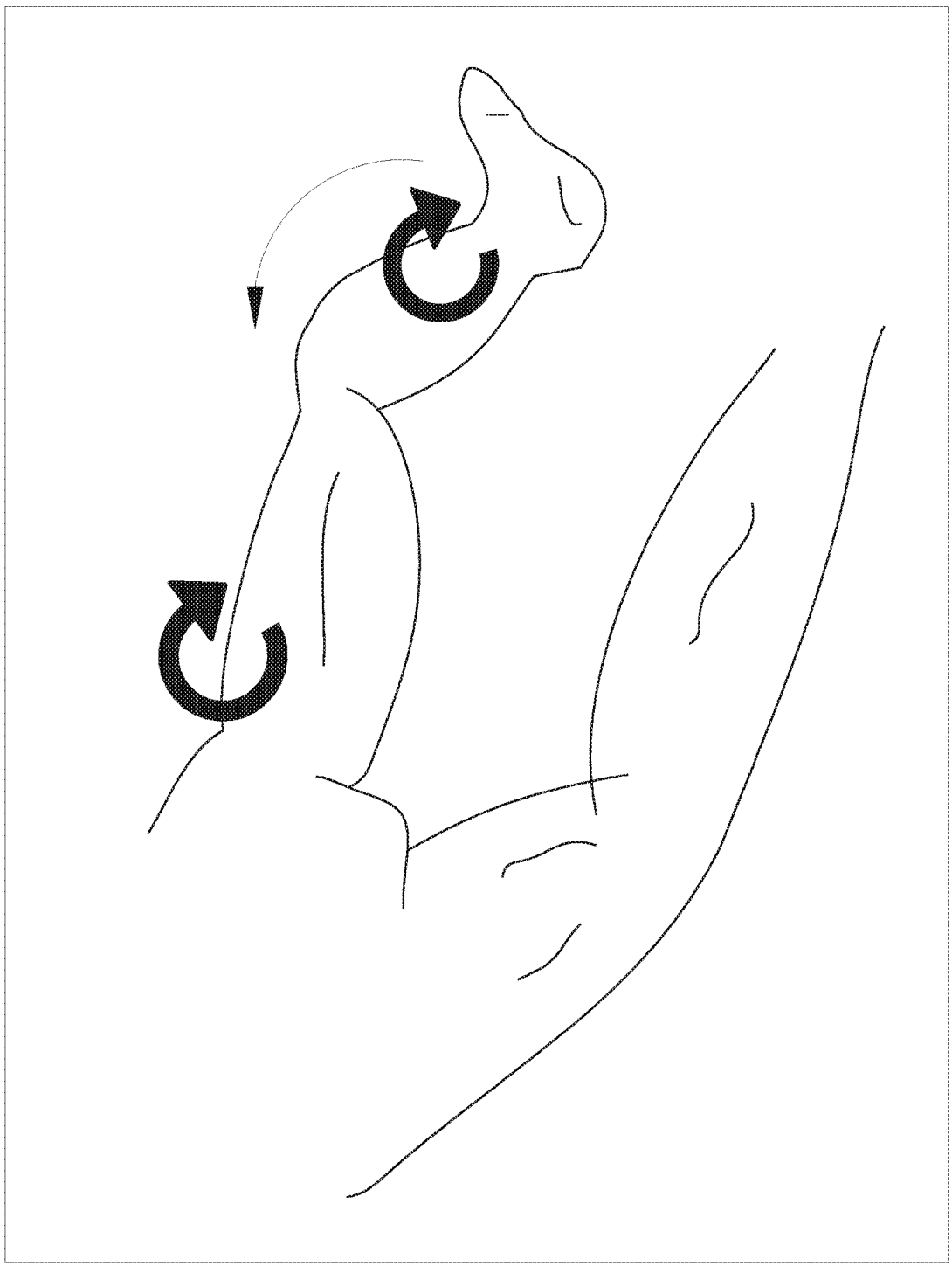

The first step of preparing the patient is shown in FIG. 12. This position allows good blood flow and good access to the user for compressing the veins during the examination.

Next the user prepares the probe by covering the tip with gel. The gel ensures good transmission of the ultrasonic waves and must usually be replenished during the examination.

Optionally, the test will comprise an examination of the common femoral vein (in the groin), the popliteal fossa (at the knee), the superficial femoral vein (in the thigh) and the saphenous veins (in the calf). If all of these veins test negative for risk of DVT in both legs then the patient can be dismissed. If there is a positive test then the patient should be referred for a further scan with a specialist or other further treatment.

While the computing device disclosed as a tablet or a smartphone, other devices having a user interface and a processor such as laptops, PCs or PDAs could equally be used.

The present invention is not limited to handheld and/or cheaper ultrasound devices. The principles of the present invention could equally be practised by adding the inventive functionality to a stand-alone ultrasound imaging device such as is common in larger hospital departments.

While the embodiments of the invention focus on providing an easy-to-use device that can be used by those without specialist skill, they may be further provided with an "expert mode" in which the display of the computing device can additionally be arranged to display the actual ultrasound images. This display may include automatically generated annotation and information about the reasoning behind classification decisions. This may be useful where a user consults a more experienced colleague who does have the ability to interpret the "raw" ultrasound images.

While a user interface comprising a visible screen has been shown, other user interfaces could alternatively or additionally be used, for example an audio interface that issues verbal instructions to the user.

The invention claimed is:

1. An apparatus for diagnosing whether a blood vessel is obstructed, the apparatus comprising:
   an interface for communication with an imaging device, the imaging device including a transmitter and a receiver;
   a user interface; and
   a processor programmed to (i) analyze image content using machine learning to identify a plurality of landmarks along a blood vessel,
(ii) inform a user, via the user interface, where to place the imaging device on a patient's body,
(iii) instruct the imaging device to transmit radiation from a probe,
(iv) receive reflected radiation information from the imaging device,
(v) interpret the reflected radiation information using a learned algorithm,
(vi) determine from the reflected radiation information whether the imaging device is located correctly relative to a blood vessel of the patient,
(vii) inform the user, if the imaging device is not located correctly, to reposition the imaging device and to repeat operations (iii) (vi) until the imaging device is correctly located,
(viii) inform the user to move longitudinally along the blood vessel with the imaging device until a landmark of the plurality of landmarks is identified;
(ix) inform the user to apply pressure to the patient's blood vessel over the landmark using the imaging device,
(x) instruct the imaging device to transmit further radiation,
(xi) receive further reflected radiation information from the imaging device,
(xii) determine from at least the further reflected radiation information whether the blood vessel is obstructed at the landmark;
(xiii) in response to determining from the further reflected radiation that the blood vessel is not obstructed at the landmark, inform the user to advance the imaging device to the next landmark of the plurality of landmarks, and
(xiv) repeat operations (ix) (xiii) one or more times to sequentially move the imaging device in a longitudinal direction between corresponding one or more additional landmarks of the plurality of landmarks along the blood vessel.

2. The apparatus of claim 1, wherein the reflected radiation information and the further reflected radiation information received from the imaging device comprise image data.

3. The apparatus of claim 1, wherein the processor is further programmed to instruct the imaging device to transmit and receive radiation continuously.

4. The apparatus of claim 1, wherein the processor is further programmed to determine, from at least the further reflected radiation information, whether the user is applying a predetermined pressure to the patient's blood vessel, and if not, to further inform the user to move the imaging device.

5. The apparatus of claim 1, further comprising the imaging device.

6. The apparatus of claim 1, wherein the imaging device is configured to transmit ultrasound signals.

7. The apparatus of claim 1, wherein the processor is programmed to determine whether the blood vessel is obstructed using one or more of: machine learning and/or deep learning algorithms.

8. The apparatus of claim 1, in which the processor is further programmed to provide ultrasound images directly to the user interface.

9. A non-transitory computer-readable medium comprising instructions that when executed by one or more processors or processing logic of a device having an imaging probe and a user interface, cause a process to be carried out for diagnosing blood vessel obstruction, the process comprising:
(i) inform a user, via the user interface, where to place the imaging probe on a patient's body;
(ii) instruct the probe to transmit radiation from the probe;
(iii) receive reflected radiation information from the probe;
(iv) determine from the reflected radiation information whether the probe is located correctly relative to a blood vessel of the patient;
(v) inform the user, if the imaging probe is not located correctly, to reposition the imaging probe and repeat operations (ii)-(iv) until the probe is correctly located;
(vi) inform the user to move longitudinally along the blood vessel with the imaging device until a landmark of a plurality of predetermined landmarks is identified;
(vii) inform the user to apply pressure to the patient's blood vessel over the landmark using the probe;
(viii) instruct the probe to transmit further radiation;
(ix) receive further reflected radiation information from the probe;
(x) determine from at least the further reflected radiation information whether the blood vessel is obstructed at the landmark;
(xi) in response to determining from the further reflected radiation that the blood vessel is not obstructed at the landmark, inform the user to advance the imaging device to the next landmark of the plurality of landmarks; and
(xii) repeat operations (vii)-(xi) one or more times to sequentially move the imaging device in a longitudinal direction between corresponding one or more additional landmarks of the plurality of predetermined landmarks along the blood vessel.

10. A method of diagnosing blood vessel obstruction using an imaging probe and a computing device in communication with the imaging probe, which computing device includes a user interface, the method comprising:
(i) informing, using the computing device, a user where to place the imaging probe on a patient's body;
(ii) transmitting radiation from the probe;
(ii) receiving reflected radiation at the probe;
(iv) determining, using the computing device, from the reflected radiation whether the imaging probe is located correctly relative to a blood vessel of the patient;
(v) if the imaging probe is not located correctly, informing, using the computing device, the user to reposition the imaging probe and repeating operations (ii)-(iv) until the probe is correctly located;
(vi) informing, using the computing device, the user to move longitudinally along a length of the blood vessel with the imaging device until a landmark of a plurality of predetermined landmarks is identified;
(vii) informing, using the computing device, the user to apply pressure to the patient's blood vessel over the landmark using the probe;
(viii) transmitting further radiation from the probe;
(ix) receiving further reflected radiation at the probe;
(x) determining, using the computing device, from at least the further reflected radiation whether the blood vessel is obstructed at the landmark;
(xi) in response to determining from the further reflected radiation that the blood vessel is not obstructed at the landmark, inform the user to advance the imaging device to the next landmark of the plurality of landmarks; and (xii) repeating operations (vii)-(xi) one or more times to sequentially move the imaging device in a longitudinal direction between corresponding one or more additional landmarks of the plurality of predetermined landmarks along the blood vessel.

11. The method of claim 10, wherein the radiation transmitted from the probe is ultrasound radiation.

12. The method of claim 10, wherein the radiation is transmitted continuously throughout the diagnosis.

13. The method of claim 10, further comprising determining, using the computing device, from the further reflected radiation, whether the user is applying the correct pressure to the patient's blood vessel, and if not, repeating the pressure informing prior to determining whether the blood vessel is obstructed.

14. The method of claim 10, wherein determining whether the blood vessel is obstructed is conducted by using one or more of: machine learning and/or deep learning algorithms.

15. A method of diagnosing blood vessel obstruction using the apparatus of claim 1, the method comprising:
preparing the patient for the diagnosis;
preparing the probe for the diagnosis;
placing the probe on the patient at a location instructed by the apparatus;
moving the probe on the patient as instructed by the apparatus;
compressing the blood vessel of the patient as instructed by the apparatus; and obtaining from the apparatus an indication as to whether blood vessel obstruction is suspected.

16. A method of diagnosing blood vessel obstruction using the apparatus of claim 1, comprising the use of Doppler Imaging to determine one or more of: blood flow speed and/or direction of blood flow.

17. The method as claimed in claim 10, wherein the reflected radiation and the further reflected radiation received at the imaging device comprise image data.

18. The method as claimed in claim 10, further comprising providing ultrasound images directly to the user interface.

19. The apparatus as claimed in claim 1, wherein the interface is configured to communicate wirelessly with the imaging device.

20. The apparatus as claimed in claim 7, wherein the machine learning and/or deep learning algorithms use a neural network.

* * * * *